US00PP16537P2

(12) United States Plant Patent
Smith

(10) Patent No.: US PP16,537 P2
(45) Date of Patent: May 16, 2006

(54) ***CHRYSANTHEMUM* PLANT NAMED 'ZESTY YOVANESSA'**

(50) Latin Name: *Chrysanthemum×morifolium*
Varietal Denomination: Zesty Yovanessa

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 55 days.

(21) Appl. No.: 10/764,865

(22) Filed: Jan. 26, 2004

(51) Int. Cl.
*A01H 5/00* (2006.01)

(52) U.S. Cl. ..... Plt./287

(58) Field of Classification Search ..... Plt./292, Plt./287, 293
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Chrysanthemum* plant named 'Zesty Yovanessa', characterized by its upright and somewhat outwardly spreading plant habit; freely branching habit; dense and full plant habit; uniform and freely flowering habit; decorative-type inflorescences with elongated oblong-shaped ray florets; light red purple-colored ray florets; and natural season flowering in mid October in the Northern Hemisphere.

2 Drawing Sheets

Botanical classification/cultivar designation: *Chrysanthemum×morifolium* cultivar Zesty Yovanessa.

BACKGROUND OF THE INVENTION

The present invention relates to a new and distinct cultivar of *Chrysanthemum* plant, botanically known as *Chrysanthemum×morifolium,* commercially known as a garden-type *Chrysanthemum* and hereinafter referred to by the name 'Zesty Yovanessa'.

The new cultivar is a product of a planned breeding program conducted by the Inventor in Alva, Fla. The objective of the breeding program is to create new garden-type *Chrysanthemum* cultivars having inflorescences with desirable inflorescence forms, attractive floret colors and good garden performance.

The new *Chrysanthemum* is a naturally-occurring whole plant mutation of the *Chrysanthemum×morifolium* cultivar Yovanessa, disclosed in U.S. Plant Pat. No. 13,825. The new *Chrysanthemum* was discovered and selected by the Inventor as a single flowering plant from within a population of plants of the cultivar Yovanessa in a controlled environment in Alva, Fla. in April, 2002. The selection of this plant was based on its desirable inflorescence form, attractive ray floret color and good garden performance.

Asexual reproduction of the new cultivar by terminal vegetative cuttings in a controlled environment in Alva, Fla. since June, 2002, has shown that the unique features of this new *Chrysanthemum* are stable and reproduced true to type in successive generations.

SUMMARY OF THE INVENTION

The cultivar Zesty Yovanessa has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Zesty Yovanessa'. These characteristics in combination distinguish 'Zesty Yovanessa' as a new and distinct cultivar:

1. Upright and somewhat outwardly spreading plant habit.
2. Freely branching habit; dense and full plants.
3. Uniform and freely flowering habit.
4. Decorative-type inflorescences with elongated oblong-shaped ray florets.
5. Light red purple-colored ray florets.
6. Natural season flowering in mid October in the Northern Hemisphere.

In side-by-side comparisons conducted in Alva, Fla., plants of the new *Chrysanthemum* differed from plants of the parent, the cultivar Yovanessa, primarily in ray floret coloration as plants of the cultivar Yovanessa had lavender-colored ray florets. In addition, plants of the new *Chrysanthemum* flowered one day later than plants of the cultivar Yovanessa when grown under natural season conditions.

Plants of the new *Chrysanthemum* differ from plants of the cultivar Bold Yovanessa, disclosed in U.S. Plant patent application Ser. No. 10/764,864, primarily in ray floret coloration. In addition, plants of the new *Chrysanthemum* were slightly smaller, but had larger inflorescences than plants of the cultivar Bold Yovanessa.

Plants of the new *Chrysanthemum* can be compared to plants of the *Chrysanthemum* cultivar Yopam, disclosed in U.S. Plant Pat. No. 11,844. In side-by-side comparisons conducted in Alva, Fla., plants of the new *Chrysanthemum* differed from plants of the cultivar Yopam in the following characteristics:

1. Plants of the new *Chrysanthemum* were more outwardly spreading than plants of the cultivar Yopam.
2. Plants of the new *Chrysanthemum* had smaller inflorescences than plants of the cultivar Yopam.
3. Ray florets of plants of the new *Chrysanthemum* did not fade as readily as ray florets of plants of the cultivar Yopam.

Plants of the new *Chrysanthemum* can also be compared to plants of the *Chrysanthemum* cultivar Lovebird, disclosed in U.S. Plant Pat. No. 11,301. In side-by-side comparisons conducted in Alva, Fla., plants of the new *Chrysanthemum* differed from plants of the cultivar Lovebird in the following characteristics:

1. Plants of the new *Chrysanthemum* were more rounded than plants of the cultivar Lovebird.
2. Plants of the new *Chrysanthemum* had smaller inflorescences than plants of the cultivar Lovebird.
3. Ray florets of plants of the new *Chrysanthemum* did not fade as readily as ray florets of plants of the cultivar Lovebird.
4. Plants of the new *Chrysanthemum* flowered about ten days later than plants of the cultivar Lovebird when grown under natural season conditions.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering plant of 'Zesty Yovanessa' grown in a container.

The photograph on the second sheet comprises a close-up view of typical inflorescences of the cultivar 'Zesty Yovanessa'.

DETAILED BOTANICAL DESCRIPTION

In the following description, color references are made to The Royal Horitcultural Society Colour Chart, 1995 Edition, except where general terms of ordinary dictionary significance are used. The following observations and measurements describe plants grown in Alva, Fla. during the winder in a fiberglass-covered greenhouse under conditions and practices which approximate those generally used in commercial garden-type *Chrysanthemum* production. One cutting was planted in a 15.25-cm container in early December, 2002. Plants were pinched one time, that is, the terminal apex was removed to enhance branching, at the end of December. One week after the pinch, plants were exposed to short day/long night photoperiodic treatments until flowering. During the production of the plants, day temperatures averaged 26° C. and night averaged 18° C. Measurements and numerical values represent averages for typical flowering plants.

Botanical classification: *Chrysanthemum×morifolium* cultivar Zesty Yovanessa.

Commercial classification: Decorative-type garden *Chrysanthemum*.

Parentage: Naturally-occurring whole plant mutation of the *Chrysanthemum×morifolium* cultivar Yovanessa, disclosed in U.S. Plant Pat. No. 13,825.

Propagation:

*Type.*—Terminal vegetative cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Plant form/growth habit.*—Perennial herbaceous decorative-type garden *Chrysanthemum*. Inverted triangle with mounded crown. Stems initially upright, then somewhat outwardly spreading. Freely branching with lateral branches potentially forming at every node. Moderately vigorous to vigorous.

*Plant height.*—About 22 cm.

*Plant diameter.*—About 26 cm.

*Lateral branches.*—Length: About 18 cm. Diameter: About 3 mm. Internode length: About 1.1 cm. Aspect: Upright and outwardly spreading. Texture: Pubescent. Color: Close to 146A.

*Foliage description.*—Leaf arrangement: Alternate. Length: About 3.8 cm. Width: About 3.25 cm. Apex: Mucronate. Base: Attenuate with truncate tendencies. Margin: Palmately lobed, sinuses divergent. Texture, upper surface: Slightly pubescent. Texture, lower surface: Pubescent; veins prominent. Color: Developing foliage, upper surface: 147A. Developing foliage, lower surface: Darker than 147B. Fully expanded foliage, upper surface: 147A. Fully expanded foliage, lower surface: 147B. Venation, upper surface: 147A. Venation, lower surface: 147B. Petiole length: About 2.3 cm. Petiole diameter: About 2 mm. Petiole color, upper surface: 147A to 147B. Petiole color, lower surface: 147B to 147C.

Inflorescence description:

*Appearance.*—Decorative-type inflorescence form with elongated oblong-shaped ray florets. Inflorescences borne on terminals above foliage, arising from leaf axils. Ray florets developing acropetally on a capitulum. About 13 inflorescences per lateral branch.

*Flowering response.*—Under natural season conditions, plants flower in mid October in the Northern Hemisphere.

*Inflorescence bud (before showing color).*—Height: About 4 mm. Diameter: About 6 mm. Shape: Oblate. Color (lower surface of phyllaries): Close to 147A.

*Inflorescence size.*—Diameter: About 4.6 cm. Depth (height): About 2.1 cm. Disc diameter: No disc florets observed. Receptacle diameter: About 3.5 mm.

*Ray florets.*—Shape: Elongated oblong. Length: About 2.25 cm. Corolla tube length: About 2.5 mm. Width: About 4.5 mm. Apex: Emarginate. Margin: Fused. Texture: Smooth, glabrous; satiny. Surface: Incurved to mostly flat. Orientation: Initially upright, then perpendicular to vertical. Number of ray florets per inflorescence: About 125 in numerous whorls. Color: When opening and fully opened, upper surface: Close to 155D overlain with close to 70A to 71A. When opening and fully opened, lower surface: Close to 155D underlain with close to 70A to 71A.

*Disc florets.*—None observed.

*Phyllaries.*—Quantity per inflorescence: About 20. Length: About 5 mm. Width: About 1.5 mm. Shape: Ligulate. Apex: Acute. Base: Truncate. Margin: Entire. Texture, upper surface: Smooth, waxy. Texture, lower surface: Pubescent. Color, upper surface: Close to 146A. Color, lower surface: Close to 147A.

*Peduncle.*—Length: First peduncle: About 2.5 cm. Fourth peduncle: About 4.8 cm. Seventh peduncle: About 6.4 cm. Diameter: About 1 mm. Strength: Strong. Aspect: About 45° from vertical. Texture: Pubescent. Color: Close to 146A.

*Reproductive organs.*—Gynoecium: Present on ray florets.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be tolerant to rain, wind and temperatures ranging from 0 to more than 38° C.

It is claimed:

1. A new and distinct cultivar of *Chrysanthemum* plant named 'Zesty Yovanessa', as illustrated and described.

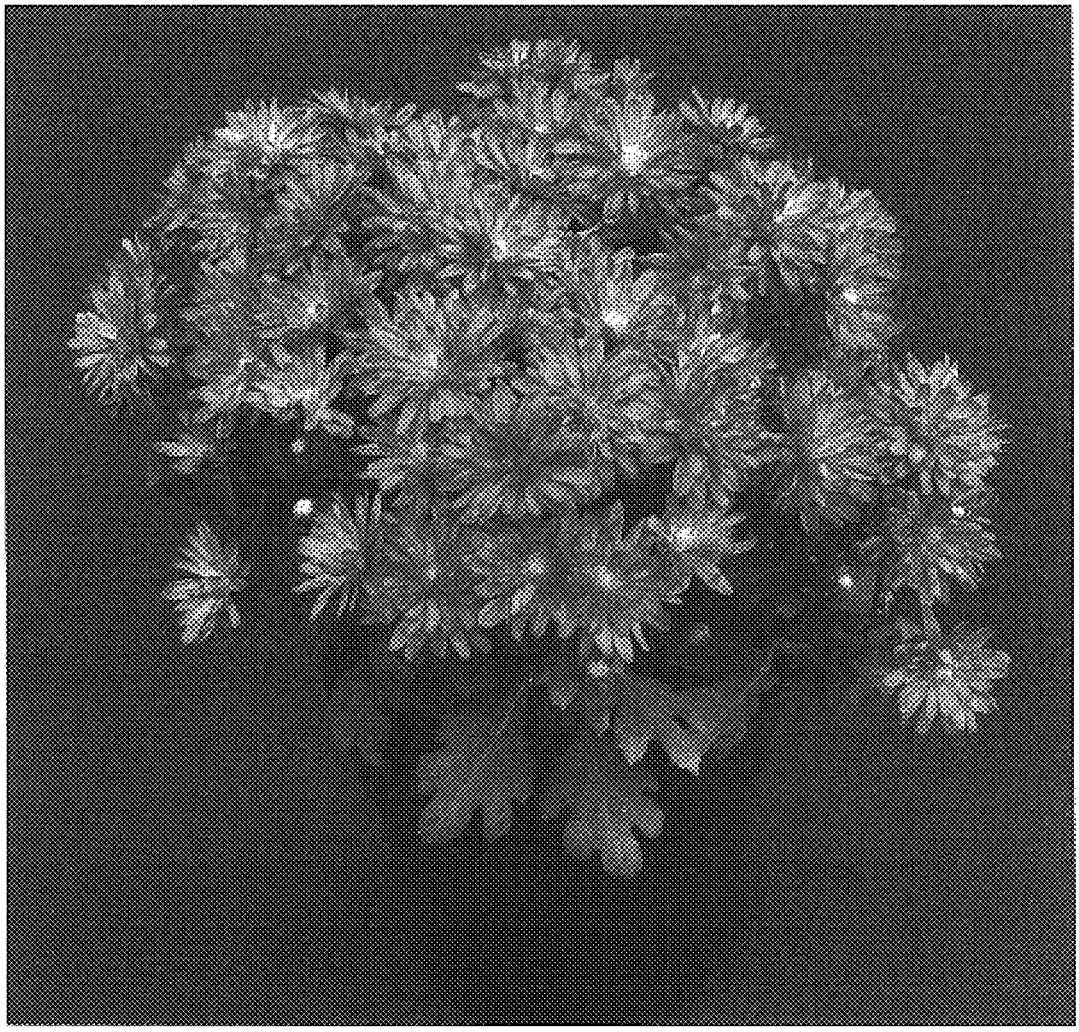

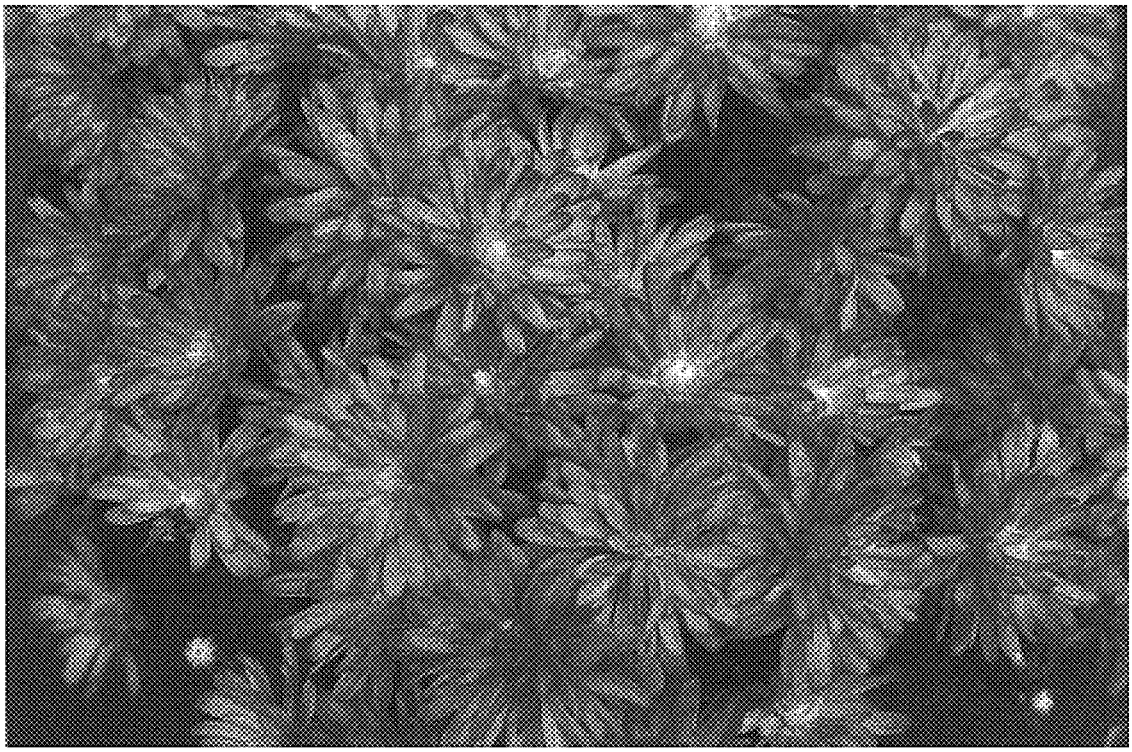

* * * * *